United States Patent [19]

Tanisake et al.

[11] Patent Number: 5,182,392

[45] Date of Patent: Jan. 26, 1993

[54] PROCESS FOR PRODUCING BISTRIMELLITIC IMIDE

[75] Inventors: Hiroka Tanisake; Takeshi Koyama; Tsuyoshi Isozaki, all of Hiratsuka, Japan

[73] Assignee: Mitsubishi Gas Chemical Company, Inc., Tokyo, Japan

[21] Appl. No.: 791,534

[22] Filed: Nov. 14, 1991

[30] Foreign Application Priority Data

Nov. 19, 1990 [JP] Japan .................................. 2-311397

[51] Int. Cl.$^5$ .......................................... C07D 207/40
[52] U.S. Cl. .................................................... 548/520
[58] Field of Search .......................................... 548/520

[56] References Cited

U.S. PATENT DOCUMENTS 3,975,330  8/1976  Suzuki et al. ....................... 548/520

FOREIGN PATENT DOCUMENTS

| 1597 | 5/1979 | European Pat. Off. | ............. 548/520 |
| 2181 | 6/1979 | European Pat. Off. | ............. 548/520 |
| 2182 | 6/1979 | European Pat. Off. | ............. 548/520 |
| 195402 | 9/1986 | European Pat. Off. | ............. 548/520 |
| 207894 | 1/1987 | European Pat. Off. | ............. 548/520 |
| 372935 | 6/1990 | European Pat. Off. | ............. 548/520 |
| 2425667 | 12/1975 | Fed. Rep. of Germany | ....... 548/520 |
| 2234289 | 1/1975 | France | ................. 548/520 |

OTHER PUBLICATIONS

CA 113:232239q Diimido . . . polymers, Tanisake et al. p. 11, Dec. 1988.

CA 113:133128w Heat-resistant . . . manufacture, Takeda et al. p. 22, Oct. 1988.

*Primary Examiner*—Mary C. Lee
*Assistant Examiner*—Joseph K. McKane
*Attorney, Agent, or Firm*—Wenderoth, Lind & Ponack

[57] ABSTRACT

A process for producing a bistrimellitic imide of the formula (2)

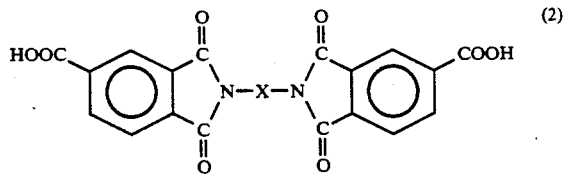

wherein X is an aliphatic group having at least 2 carbon atoms, an alicyclic group or an aromatic group, which comprises reacting a trimellitic anhydride with a diamine of the formula (1)

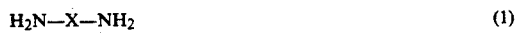

wherein X is as defined above, in the presence of a solvent mixture containing an aprotic polar solvent and an aromatic hydrocarbon solvent which can be distilled azeotropically with water, the amount of the aromatic hydrocarbon solvent being 10 to 90% by weight based on the total weight of these two solvents.

2 Claims, No Drawings

PROCESS FOR PRODUCING BISTRIMELLITIC IMIDE

DETAILED DESCRIPTION OF THE INVENTION

The present invention relates to a process for producing a bistrimellitic imide. More specifically, it relates to a process for producing a bistrimelltic imide industrially advantageously.

Bistrimellitic imides are industrially highly valued as a dicarboxylic acid component for polymers having excellent heat resistance such as polyamideimide, polyesterimide, etc.

Japanese Patent Publications Nos. 21500/1963 and 9018/1965 disclose a process for producing a bistrimellitic imide from diamine and any one of trimellitic acid, trimellitic anhydride and a derivative thereof in the presence of a solvent unreactive with these compounds, i.e., either an aprotic polar solvent or a phenolic solvent. Further, in this process, after the reaction, a formed bistrimellitic imide is precipitated while it is hot or cold, filtered, washed and dried to recover it as a product.

However, the above conventional process involves a problem that since the affinity between a bistrimellitic imide as a reaction product and the solvent is too high, a considerable amount of bistrimellitic imide remains dissolved in the solvent, and hence, the product yield is low. On the other hand, in order to increase the product yield, there may be contrived a method to recycle a filtrate. This method, however, involves a problem that it is difficult to obtain a high-purity bistrimellitic imide. Further, although it is possible to increase a product yield by distilling a solvent off from a filtrate, such a method can not be said to be industrially advantageous.

Further, conventionally known solvents generally have a high boiling point and too high affinity with bistrimellitic imide. It is therefore difficult to remove such solvents efficiently even if the crystal of bistrimellitic imide is washed with other solvent and dried under vacuum at a high temperature.

Therefore, it is an object of the present invention to provide a process for producing a bistrimellitic imide industrially advantageously.

It is another object of the present invention to provide a process for producing a bistrimellitic imide, in which the reaction can be completed for a relatively short period of time.

It is further another object of the present invention to provide a process for producing a bistrimellitic imide, in which the end product can be easily recovered after the reaction and a high-purity bistrimellitic imide can be obtained at high yields.

The other objects and advantages of the present invention will be apparent from the following description.

According to the present invention, the above objects and advantages of the present invention are achieved by a process for producing a bistrimellitic imide of the formula (2)

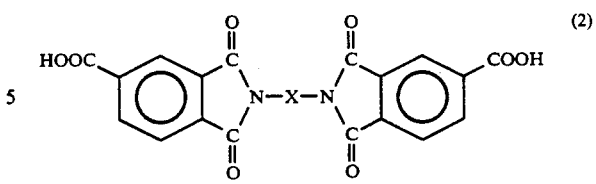

wherein X is an aliphatic group having at least 2 carbon atoms, an alicyclic group or an aromatic group, which comprises reacting a trimellitic anhydride with a diamine of the formula (1)

$$H_2N-X-NH_2 \qquad (1)$$

wherein X is as defined above, in the presence of a solvent mixture containing an aprotic polar solvent and an aromatic hydrocarbon solvent which can be distilled azeotropically with water, the amount of the aromatic hydrocarbon solvent being 10 to 90% by weight based on the total weight of these two solvents.

In the process of the present invention for producing a bistrimellitic imide, a solvent mixture containing an aprotic polar solvent and an aromatic hydrocarbon solvent is used as described above.

The present inventors' study has revealed the following: The above solvent mixture having the above-specified composition dissolves a diamine and a trimellitic anhydride which are starting materials, but does not dissolve a bistrimellitic imide which is a reaction product, and a formed bistrimellitic imide is therefore precipitated during the reaction. Due to this, the recovery and purification of the product according to the present invention are easy as compared with the conventional process. Further, since the aromatic hydrocarbon used as a solvent component can be distilled azeotropically with water, water formed during the reaction can be removed out of the reaction system. As an unexpected result, the reaction time can be decreased. The present invention has been completed on the basis of the above finding.

The acid component used in the present invention is a trimellitic anhydride.

The diamine used in the present invention has the above formula (1). In the formula (1), X is an aliphatic group having at least 2 carbon atoms, an alicyclic group or an aromatic group.

The aliphatic group having at least 2 carbon atoms may be linear or branched, and it may be interrupted by —O—, —S—, etc.

Examples of the above aliphatic group are preferably ethylene, trimethylene, tetramethylene, pentamethylene, hexamethylene, octamethylene, nonamethylene, decamethylene, 3-methylheptamethylene, 1,2-propylene, 1-methylundecamethylene, 1-hexyldodecamethylene, 2,2-dimethylpropylene, —(CH$_2$)$_3$—O—(CH$_2$)$_2$—O—(CH$_2$)$_3$—, and —(CH$_2$)$_2$—S—(CH$_2$)$_3$—.

Examples of the above alicyclic group are 1,4-cyclohexylene,

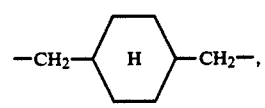

and

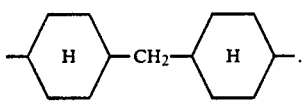

The above aromatic group may be interrupted by —O—, —S—, etc. Examples of the aromatic group are phenylene, xylylene, naphthylene, biphenylene and a group of the formula

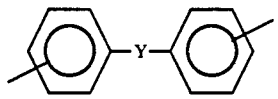

wherein Y is methylene, dimethylmethylene, —O—, —S— or —$SO_2$—.

Examples of the diamine of the above formula (1) are preferably aliphatic diamines such as ethylenediamine, trimethylenediamine, tetramethylene-diamine, pentamethylenediamine, hexamethylenediamine, heptamethylenediamine, octamethylenediamine, nonamethylenediamine, decamethylenediamine, 3-methylheptamethylenediamine, diaminopropyl, 2,11-diaminododecane, 1,12-diaminooctadecane, 2,2-dimethylpropylenediamine, $H_2N(CH_2)_3O(CH_2)_2O(CH_2)_3NH_2$ and $H_2N(CH_2)_2S(CH_2)_3NH_2$; alicyclic diamines such as 1,4'-diaminocyclohexane, 1,4-bis(aminomethyl)-cyclohexane and di-(p-aminocyclohexyl)methane; and aromatic diamines such as m-phenylenediamine, p-phenylenediamine, m-xylylenediamine, p-xylylenediamine, benzidine, 4,4'-diaminobiphenylpropane, 4,4'-diaminobiphenylmethane, 4,4'-diaminobiphenylsulfide, 3,3'-diaminobiphenylsulfone, 4,4'-diaminobiphenyl ether, 1,5-diaminonaphthalene, and 3,3-diaminonaphthalene. These diamines may be used alone or in combination of two or more.

In the process of the present invention, the diamine of the above formula (1) is allowed to react with a trimellitic anhydride in a reaction solvent.

The reaction solvent refers to a solvent mixture containing an aprotic polar solvent and an aromatic hydrocarbon which can be distilled azeotropically with water. This solvent mixture does not react with the diamine and the trimellitic anhydride.

The aprotic polar solvent used in the present invention is preferably selected, for example, from amides and sulfoxides such as dimethylacetamide, dimethylformamide, dimethylsulfoxide and N-methylpyrrolidone.

The aromatic hydrocarbon which can be distilled azeotropically with water, used in the present invention, is preferably selected from highly volatile aromatic hydrocarbons such as benzene, toluene, ethylbenzene, xylene and pseudocumene. Particularly preferred are those having a boiling point of not higher than 200° C. under atmospheric pressure.

Since the above aromatic hydrocarbons are solvents which can be distilled azeotropically with water, the present invention, first of all, can produce high-purity bistrimellitic imides.

Trimellitic anhydride is highly reactive with water, and reacts with water in air or in the solvent to form trimellitic acid easily. Trimellitic acid formed from the hydration of trimellitic anhydride reacts with a diamine to form a polyamide, which formation results in impurities. It is therefore required to reduce the water content in the reaction system as much as possible.

However, in the present invention, since the aromatic hydrocarbon which can be distilled azeotropically with water is used as a solvent, water contained in the solvent can be removed by azeotropy before the above hydration takes place. Therefore, the present invention has an advantage that polyamides as impurities are not formed or accumulated in the reaction system even when the solvent is recycled without specially controlling the water content.

Further, it has been found in the present invention that the use of the aromatic hydrocarbon which can be distilled azeotropically with water produces an effect of promoting the reaction rate.

The reason for the promotion of the reaction rate is considered to be as follows. The reaction in the present invention proceeds as an equilibrium reaction between bistrimellitic imide and an amidocarboxylic acid, and the equilibrium becomes off balance when formed water is removed out of the system by azeotropy. As a result, the reaction for forming bistrimellitic imide is promoted.

In the conventional process, too, water is removed out of the system through a partial condenser. In the present invention, however, it has been found for the first time that the removal of water by azeotropy is more effective to advance the reaction.

The mixing weight ratio for the solvent mixture used in the present invention is also critical.

The present invention uses a solvent mixture of an aprotic polar solvent and an aromatic hydrocarbon solvent which can be distilled azeotropically with water, in which the amount of the aromatic hydrocarbon solvent based on the total weight of these two solvents is 10 to 90% by weight, preferably 50 to 90% by weight.

When the amount of the aromatic hydrocarbon solvent is less than the above lower limit, the effect of precipitating bistrimellitic imide in the reaction system is decreased, and as a result, the yield of bistrimellitic imide as a product is low.

Further, the effect of removing water out of the system by azeotropy is decreased, and the effect on promotion of the reaction is also decreased.

On the other hand, when the above amount exceeds the above upper limit, an amidocarboxylic acid as a reaction intermediate precipitates and coagulates, and the reaction for forming an imido ring does not proceed.

The aromatic hydrocarbon solvent is distilled azeotropically with water during the reaction, and is removed out of the system. There is therefore a risk of the aromatic hydrocarbon solvent being decreased until the amount thereof is less than the above lower limit.

In order to maintain a constant amount of the aromatic hydrocarbon solvent in the system, therefore, it is advantageous, for example, to recycle the solvent, which has been distilled out of the system, into the system after separation of water from it with a water-separating tube, or to add a fresh solvent to the system in an amount equivalent to that of the distilled solvent.

The solvent mixture is preferably used in such an amount that the solvent mixture dissolves the starting materials such as a diamine and a trimellitic anhydride and that a bistrimellitic imide formed in the system is precipitated in the solvent mixture while it is hot or cold.

For example, the weight ratio of the solvent mixture to the diamine and trimellitic anhydride charged is at least 0.5.

When the weight ratio of the solvent mixture is less than 0.5, there is sometimes a disadvantage that an amidocarboxylic acid as a reaction intermediate precipitates and coagulates in the reaction system.

The reaction in the present invention is preferably carried out at a temperature between 20° C. and 300° C.

The reaction is carried out until no water is formed as a by-product. A formed bistrimellitic imide is insoluble, or has a low solubility, in the solvent mixture used in the present invention. Therefore, the reaction liquid is in a slurry state after a stoichiometric amount of water is completely distilled off.

Even when a small amount of a bistrimellitic imide is dissolved in the solvent, a high-purity bistrimellitic imide can be quantitatively recovered by recycling the solvent.

After the reaction, the bistrimellitic imide can be recovered at very high yields by simple procedures such as filtration, washing, drying, etc.

The so-obtained bistrimellitic imide has very high purity even if it is not subjected to any special treatment.

The above bistrimellitic imide produced by the present invention has the following formula (2),

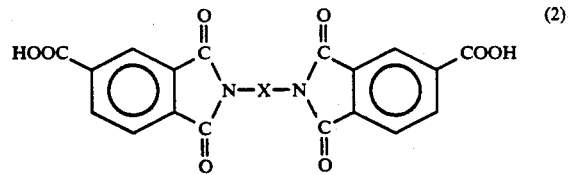

(2)

in which X is as defined previously.

According to the present invention, as described above, the reaction time is greatly decreased as compared with the conventional process, bistrimellitic imide is precipitated in the reaction system, and the procedures for recovery and purification of the bistrimellitic imide are eased as compared with the conventional process. The conditions for drying a crystal of the bistrimellitic imide are improved, and a high-purity bistrimellitic imide can be obtained.

The present invention will be specifically described hereinafter by reference to Examples. However, the present invention shall not be limited to these Examples.

In Examples and Comparative Examples, bistrimellitic imides were measured for an acid value as follows.

That is, about 100 mg of a bistrimellitic imide was taken into a 100 ml beaker, and 20 ml of dimethylformamide was added. The mixture was stirred to form a solution, and the solution was subjected to titration with 1/10N KOH.

EXAMPLE 1

A one-liter four-necked separable flask having a water-separating tube, a thermometer and a nitrogen-introducing tube was charged with 96 g (0.5 mol) of trimellitic anhydride, 100 g of dimethylformamide and 268 g of m-xylene, and while the mixture was stirred, the temperature in the flask was raised to 140° C.

Around 100° C., the trimellitic anhydride was dissolved. When the temperature reached 140° C., the solvent was refluxed, and the temperature became constant.

Then, 34.4 g (0.25 mol) of p-xylylenediamine was added dropwise.

According as the p-xylylenediamine was added dropwise, an amidocarboxylic acid was formed as a yarn-like white precipitate, and it was gradually dissolved.

Refluxing occurred violently due to an exothermic reaction, and after a while, water formed due to the imidation was distilled azeotropically with m-xylene, and the water was condensed in the water-separating tube.

Water was collected in the separating tube bottom, since water has a higher specific gravity than m-xylene. And m-xylene alone was overflowed and recycled to the reactor. According as the amount of the collected water increased, a white particulate precipitate was again formed.

Further, the reaction was continued, and when no distillation of water was observed, the reaction was terminated.

The time required for the reaction was 1.5 hours.

After the reaction, the reaction liquid at room temperature was in a slurry state which was caused by the precipitation of a white crystal.

The above reaction liquid was filtered, and the remaining solid was fully washed with ethanol, and dried under reduced pressure to give 108 g of a white crystal of 1,3-bis(N-trimellitic imide methyl)benzene.

The yield of the above product based on the p-xylylenediamine was 89 mol %.

The acid value thereof was 230.6 mgKOH/g (99.5% of the stoichiometric value).

EXAMPLE 2

The experiment on recycle of the solvent was carried out by the use of the same flask as that used in Example 1 and the filtrate obtained in Example 1, and by adding fresh solvents so that the same solvent mixing ration and the same solvent amounts as those described in Example 1 were attained.

The flask was charged with 96 g (0.5 mol) of trimellitic anhydride, and the temperature in the flask was raised to 140° C. with stirring.

Then, 34.4 g (0.25 mol) of p-xylylenediamine was added.

Water formed due to the imidation was distilled azeotropically with xylene, and the water was condensed in the water-separating tube.

According as the amount of the water increased, a white particulate precipitate was again formed. The reaction was continued, and when no distillation of water was found, the reaction was terminated.

The time required for the reaction was 1.5 hours.

After the reaction, the reaction liquid at room temperature was in a slurry state which was caused by the precipitation of a white crystal.

The above reaction liquid was filtered, and the remaining solid was fully washed with ethanol and dried under reduced pressure to give 119 g of a white crystal of 1,3-bis(N-trimellitic imide methyl)benzene. The yield of the above product based on the p-xylylenediamine was 98 mol %.

The acid value thereof was 232.3 mgKOH/g (100% of the stoichiometric value).

The above experiment on recycle of the solvent has shown that a high-purity bistrimellitic imide can be nearly quantitatively obtained.

COMPARATIVE EXAMPLE 1

A one-liter four-necked separable flask having a partial condenser, a thermometer and a nitrogen-introducing tube was charged with 96 g (0.5 mol) of trimellitic anhydride and 368 g of dimethylformamide, and the mixture was dissolved at 100° C. with stirring.

Then, 34.4 g (0.25 mol) of p-xylylenediamine was added.

An increase by about 10° C. was observed due to an exothermic reaction, and the temperature of the mixture was immediately raised to 150° C. to start the reaction.

Distillation of water formed due to the imidation started. The water formed was removed out of the system through the partial condenser. The reaction was further continued, and when no distillation of water was observed, the reaction was terminated.

The time required for the reaction was 6 hours.

After the reaction, the reaction liquid showed no precipitation of a crystal, and it was a uniform solution. Five hundred grams of water was added to the reaction liquid to precipitate a crystal. The crystal was poorly filtered, and the filtering took a long time. The resultant crystal was fully washed with ethanol, and dried under reduced pressure to give 116 g of a yellowish crystal. The yield of the above product based on the p-xylylenediamine was 96.5 mol %.

The acid value of thereof was 224.4 mgKOH/g (96.8% of the stoichiometric value).

In comparison with the results of Example 1, the reaction time was doubled due to the use of only dimethylformamide having high solubility for the reaction, and therefore, no high-purity bistrimellitic imide was obtained. Further, the dried crystal emitted the odor of the dimethylformamide solvent to some extent.

COMPARATIVE EXAMPLE 2

A one-litter four-necked separable flask having a water-separating tube, a thermometer and a nitrogen-introducing tube was charged with 96 g (0.5 mol) of trimellitic anhydride and 368 g of m-xylene, and while the mixture was stirred, the temperature inside the flask was raised to 140° C. Then, 34.4 g (0.25 mol) of p-xylylenediamine was added.

According as the p-xylylenediamine was added, an amidocarboxylic acid was formed as a yarn-like white precipitate. The precipitate was gradually formed into a mass without being dissolved, which mass finally permitted no stirring.

Even when the reaction was continued at 140° C. with the reaction product as a mass, no formation of water taking place due to the imidation was observed.

In comparison with the results of Example 1, the reaction did not proceed due to the use of only m-xylene having low solubility, and no bistrimellitic imide was obtained.

EXAMPLE 3

A one-litter four-necked separable flask having a water-separating tube, a thermometer and a nitrogen-introducing tube was charged with 96 g (0.5 mol) of trimellitic anhydride, 100 g of dimethylformamide and 268 g of m-xylene, and the mixture was heated under stirring.

Around the temperature of 100° C., the trimellitic anhydride was dissolved. When the temperature inside the flask reached 140° C., the solvent was refluxed, and the temperature became constant.

Then, 50 g (0.25 mol) of a powder of 4,4'-diaminobiphenyl ether was added.

With addition of the 4,4'-diaminobiphenyl ether, and amidocarboxylic acid was formed, and dissolved to form a brown solution.

After a while, water formed due to the imidation was distilled azeotropically with m-xylene, and condensed in the water-separating tube, and the precipitation of a crystal started.

Water was collected in the separating tube bottom, since water has a higher specific gravity than m-xylene. And m-xylene alone was overflowed and recycled to the reactor. According as the amount of the collected water increased, a yellow particulate precipitate was again formed.

The reaction was continued, and when no distillation of water was found, the reaction was terminated.

The time required for the reaction was 1.5 hours.

After the reaction, the reaction liquid was in a slurry state caused by the precipitation of a yellow crystal.

The above reaction liquid was filtered, and the remaining solid was fully washed with ethanol and dried under reduced pressure to give 119 g of the yellow crystal of 4,4-bis(N-trimellitic imide methyl)biphenyl ether.

The yield of the above product based on the 4,4'-diaminobiphenyl ether was 87 mol %.

The acid value thereof was 204.8 mgKOH/g (100% of the stoichiometric value).

COMPARATIVE EXAMPLE 3

A one-liter four-necked separable flask having a partial condenser, a thermometer and a nitrogen-introducing tube was charged with 96 g (0.5 mol) of trimellitic anhydride and 368 g of dimethylformamide, and the trimellitic anhydride was dissolved at 100° C. with stirring.

Then, 34.4 g (0.25 mol) of 4,4'-diaminobiphenyl ether was added.

An increase in temperature by about 10° C. was observed, and the temperature inside the flask was immediately raised to 150° C. to start the reaction. The distillation of water formed by the imidation started. The water was removed out of the system through the partial condenser.

The reaction was continued, and when no distillation of water was found, the reaction was terminated.

The time required for the reaction was 6 hours.

After the reaction, the reaction liquid was in a slurry state caused by the precipitation of a yellow crystal. The above reaction liquid was filtered, and the remaining solid was fully washed with ethanol and dried under reduced pressure to give 111 g of a yellowish crystal.

The yield of the above product based on the 4,4'-diaminobiphenyl ether was 81 mol %.

The acid value thereof was 198.2 mgKOH/g (96.8% of the stoichiometric value).

In comparison with the results of Example 3, the reaction time was doubled due to the use of only dimethylformamide having high solubility for the reaction, and therefore, no high-purity bistrimellitic imide was obtained.

Further, the dried crystal emitted the odor of the dimethylformamide solvent to some extent.

What is claimed is:

1. A process for producing a bistrimellitic imide of the formula (2)

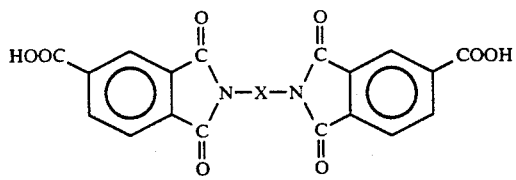

wherein X is an aliphatic group having at least 2 carbon atoms, an alicyclic group or an aromatic group, which comprises reacting a trimellitic anhydride with a diamine of the formula (1)

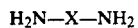

wherein X is as defined above, in the presence of a solvent mixture containing an aprotic polar solvent and an aromatic hydrocarbon solvent which can be distilled azeotropically with water while water formed as a byproduct is removed with the aromatic hydrocarbon by azeotropic distillation and the bistrimellitic imide formed is precipitated in the reaction system, the amount of the aromatic hydrocarbon solvent being 10 to 90% by weight based on the total weight of these two solvents.

2. The process of claim 1, wherein the aromatic hydrocarbon is isolated from the azeotrope mixture of water and the aromatic hydrocarbon and recycled to the reaction system.

* * * * *